United States Patent
Henning et al.

(10) Patent No.: US 12,168,053 B2
(45) Date of Patent: Dec. 17, 2024

(54) MICRONEEDLE SYSTEM FOR APPLYING A HEPATITIS VACCINE

(71) Applicant: LTS LOHMANN THERAPIE-SYSTEME AG, Andernach (DE)

(72) Inventors: Andreas Henning, Koblenz (DE); Heiko Spilgies, Koblenz (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 363 days.

(21) Appl. No.: 16/762,539

(22) PCT Filed: Nov. 12, 2018

(86) PCT No.: PCT/EP2018/080986
§ 371 (c)(1),
(2) Date: May 8, 2020

(87) PCT Pub. No.: WO2019/092257
PCT Pub. Date: May 16, 2019

(65) Prior Publication Data
US 2021/0369839 A1 Dec. 2, 2021

(30) Foreign Application Priority Data
Nov. 10, 2017 (DE) ............ 10 2017 126 501.5

(51) Int. Cl.
*A61K 39/29* (2006.01)
*A61K 47/10* (2017.01)
(Continued)

(52) U.S. Cl.
CPC ............. *A61K 39/29* (2013.01); *A61K 47/10* (2013.01); *A61K 47/26* (2013.01); *A61K 47/32* (2013.01);
(Continued)

(58) Field of Classification Search
None
See application file for complete search history.

(56) References Cited

U.S. PATENT DOCUMENTS 6,589,202 B1 * 7/2003 Powell ............. A61M 37/0015
604/890.1
10,792,042 B2 * 10/2020 Matonick ......... A61B 17/07292
(Continued)

FOREIGN PATENT DOCUMENTS

CN 104027324 A 9/2014
DE 10353629 A1 6/2005
(Continued)

OTHER PUBLICATIONS

EPAR zu hbvaxpro, abgerufen am Aug. 12, 2020 unter https://www.ema.europa.eu/en/medicines/human/EPAR/hbvaxpro, zuletzt aktualisiert am Jul. 25, 2011.
(Continued)

*Primary Examiner* — Lakshmi S Channavajjala
(74) *Attorney, Agent, or Firm* — Faegre Drinker Biddle & Reath LLP

(57) ABSTRACT

The present invention relates to a microneedle system (MNS for short) for the intradermal application of a hepatitis vaccine, namely the antigen HBsAg.

13 Claims, 1 Drawing Sheet

(51) Int. Cl.
  *A61K 47/26* (2006.01)
  *A61K 47/32* (2006.01)
  *A61M 37/00* (2006.01)
  *A61K 9/00* (2006.01)

(52) U.S. Cl.
  CPC ....... *A61M 37/0015* (2013.01); *A61K 9/0021* (2013.01); *A61M 2037/0023* (2013.01); *A61M 2037/003* (2013.01); *A61M 2202/30* (2013.01)

(56) References Cited

U.S. PATENT DOCUMENTS

| | | | |
|---|---|---|---|
| 2004/0049150 A1 | 3/2004 | Dalton et al. | |
| 2007/0081977 A1 | 4/2007 | Horstmann | |
| 2007/0106207 A1* | 5/2007 | Withey | A61M 37/0015 435/173.6 |
| 2009/0041810 A1 | 2/2009 | Andrianov et al. | |
| 2009/0155330 A1 | 6/2009 | Ghartey-Tagoe et al. | |
| 2013/0123707 A1 | 5/2013 | Determan et al. | |
| 2015/0057604 A1* | 2/2015 | Arami | A61M 37/0015 29/428 |
| 2017/0065534 A1* | 3/2017 | Sawicka | C07K 16/00 |
| 2018/0193256 A1 | 7/2018 | Kabata et al. | |

FOREIGN PATENT DOCUMENTS

| | | |
|---|---|---|
| DE | 60131688 T2 | 10/2008 |
| EP | 3085357 A1 | 10/2016 |
| EP | 3348256 A1 | 7/2018 |
| EP | 3412312 A1 | 12/2018 |
| JP | 2010-516337 A | 5/2010 |
| JP | 2012041329 A | 3/2012 |
| JP | 2017-051312 A | 3/2017 |
| JP | 2017-137311 A | 8/2017 |
| KR | 10-2017-0032810 A | 3/2017 |
| WO | WO-200189622 A1 | 11/2001 |
| WO | WO-200219985 A2 | 3/2002 |
| WO | 2008/091602 A2 | 7/2008 |
| WO | WO-2011150144 A3 * | 6/2012 ............ A61K 47/32 |
| WO | 2017/043517 A1 | 3/2017 |

OTHER PUBLICATIONS

International Preliminary Examination Report for PCT/EP2018/080986 mailed Feb. 25, 2020.
International Search Report for PCT/EP2018/080986 mailed Feb. 18, 2019.
Kim, Y-C., et al., "Microneedles for drug and vaccine delivery", Advanced Drug Delivery Reviews, vol. 64, No. 14, (2012), pp. 1547-1568.
Poirier, D., et al., "Hepatitis B surface antigen incorporated in dissolvable microneedle array patch is antigenic and thermostable", Biomaterials, vol. 145, (2017), pp. 256-265.
Sangare, L., et al., "Intradermal hepatitis B vaccination: A systematic review and meta- analysis", Vaccine, vol. 27, No. 12, (2009), pp. 1777-1786.
Written Opinion of the International Searching Authority for PCT/EP2018/080986 mailed Feb. 18, 2019.
Zhao, J., et al., "Enhanced immunization via dissolving microneedle array-based delivery system incorporating subunit vaccine and saponin adjuvant", International Journal of Nanomedicine vol. 12, (2017), pp. 4763-4772.

* cited by examiner

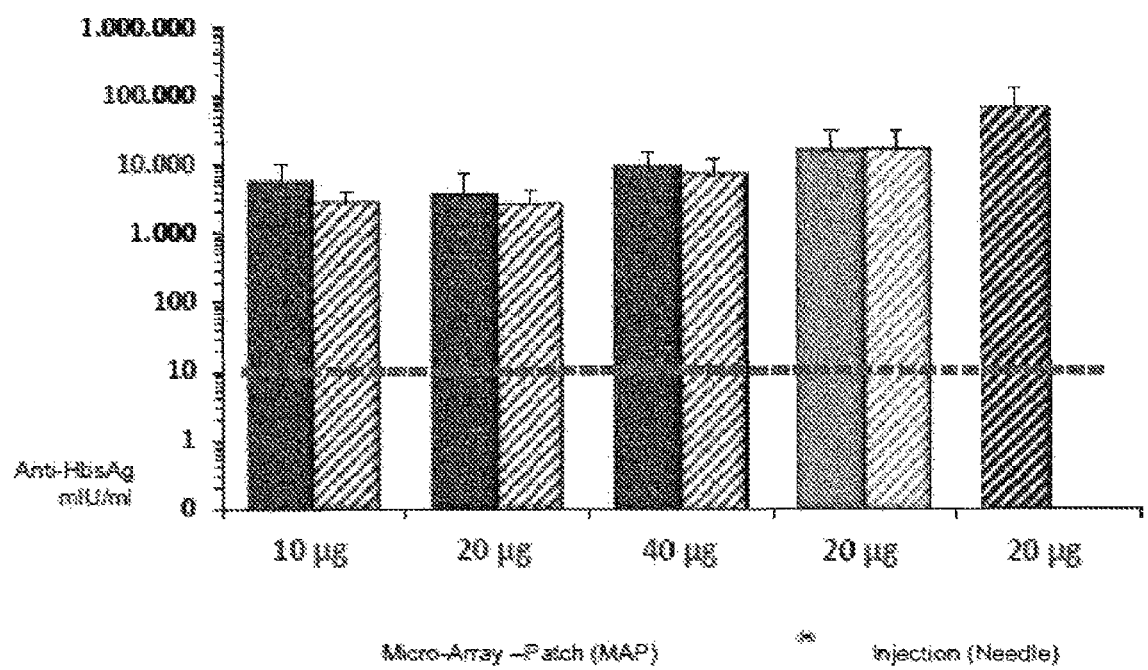

MICRONEEDLE SYSTEM FOR APPLYING A HEPATITIS VACCINE

CROSS-REFERENCE TO RELATED APPLICATIONS

This application is a national stage application (under 35 U.S.C. § 371) of PCT/EP2018/080986, filed Nov. 12, 2018, which claims benefit of German Application No. 10 2017 126 501.5, filed Nov. 10, 2017, both of which are incorporated herein by reference in their entirety.

The present invention relates to a microneedle system (MNS for short) for intradermal application of a hepatitis vaccine, namely the antigen HBsAg.

Hepatitis vaccines may contain HBsAg. HBsAg is a surface protein in the viral envelope of the hepatitis B virus (HBV, 226 AA, 25.4 kDa, see database UniProt: Q773S4). HBsAg is additionally the most effective component in the approved hepatitis B vaccines (e.g. Engerix-B, Fendrix, HBVAXPRO and many others). HBsAG is a transmembrane protein with five membrane passages and three disulphide bridges on the outside of the membrane. At the same time, it is an antigen against which neutralising antibodies are formed during a hepatitis infection or after a hepatitis vaccination. HBsAGs are also used in the form of virus-like particles (VLP) and do not contain nucleic acids (E. V. Grgacic and D. A. Anderson: Virus-like particles: passport to immune recognition. In Methods. 2006 September; 40(1): 60-5).

The skin consists of several layers. The outermost skin layer, the stratum corneum, has known barrier properties to prevent foreign substances from entering the body and to prevent the escape of inherent substances from the body. The stratum corneum, which is a complex structure of compacted keratotic cell residues with a thickness of approximately 10-30 micrometres, forms a waterproof membrane to protect the body. The natural impermeability of the stratum corneum prevents most pharmaceutical agents and other substances from being applied through the skin by intradermal application. Langerhans cells are found throughout the basal granular layer of the epithelium and play an important role in the initial defence of the immune system against invading organisms. This layer of the skin constitutes a suitable target zone for certain types of vaccines, such as the hepatitis antigen HBsAg.

Microneedle systems (MNS), which consist of a microneedle array (MNA) and possibly further components, can use a compressive force to press the microneedles (also: skin penetrating elements) of the array (MNA) against the application site on the skin in order to penetrate the stratum corneum and thus create a fluid channel so that a hepatitis vaccine can be applied intradermally. Such microneedle arrays (MNA) in microneedle systems (MNS) as well as their manufacture are described in the prior art and are also described as micro(needle) array patches (MAP, or "Micro Array Patch").

It is also known that hepatitis vaccines can be administered via microneedles (for example DE60131688T2, WO200189622A1, WO200219985A2).

Therefore, it is the object of the present invention to enable an intradermal application for vaccination by means of an MNS containing an MNA on the basis of a suitable formulation.

Surprisingly, polyvinylpyrrolidone (PVP for short) is particularly suitable for the production of a formulation for an MNA for hepatitis vaccination.

This object is achieved in accordance with the invention by a microneedle array (MNA) according to claim 1, comprising a formulation of polyvinylpyrrolidone and HBsAg for use in intradermal application for hepatitis vaccination.

The invention therefore also relates to a microneedle system containing an MNA for use in intradermal application for hepatitis vaccination, comprising a formulation of polyvinylpyrrolidone and HBsAg.

Therefore, the invention comprises a product having a microneedle array comprising or consisting of a formulation of substantially polyvinylpyrrolidone and HBsAg.

Such a product is for example a medicinal product, in particular a vaccine, comprising a protruding microneedle array (MNA) for use in intradermal application for hepatitis vaccination.

The basic requirement for successful immunisation against hepatitis B is the generation of a sufficiently high antibody concentration (titre) in the body or blood (plasma) of the vaccinated persons. As a serological target value, an anti-HBsAg titre of >10 [mLU/mL] is recognised by the WHO as clinically protective (see FIG. 1).

Especially preferred is a microneedle array according to the invention which has a HBsAg content of 0.1 μg to 100 μg per microneedle array.

The term "intradermal application" (synonym: "intracutaneous application") describes the administration of vaccines, here: HBsAg from the MNA into the skin and requires the insertion of microneedles into the skin.

The invention likewise relates to a method for performing an intradermal application for use in the intradermal application for hepatitis vaccination comprising a) fixing a microneedle system according to the invention to the skin, b) penetrating a microneedle array comprising a formulation of PVP and HBsAg into the skin.

In the context of this invention, a microneedle system is such a system which includes a device which causes the microneedle array for the administration of vaccines to be provided on the skin and applied intradermally.

The microneedle system may include an applicator, such as a triggering device, in a preferred embodiment, which applicator is electrically or mechanically controlled. For example, the applicator may have a piston that places or applies the microneedle array on/to the skin so that the microneedles penetrate the skin.

The triggering device may, for example, comprise a pump, a syringe or a spring, so that a plunger impact with sufficient energy can be implemented. The plunger may be of any shape and nature and is primarily intended to provide the microneedle array from a first position into a second position for the administration of vaccines on the skin. The applicator may also include a push button or thread.

The microneedle array may have a plurality of microneedles to deliver a vaccine through or into the skin of a patient, with the microneedle array being applied to the patient's skin. Each of the microneedles of the microneedle array preferably has an elongate shaft with two ends, one end of the shaft being the base of the microneedle by which the microneedle is attached to the flat carrier or by which the microneedle is integrated into the flat carrier. The end of the shaft opposite the base is preferably tapered to allow the microneedle to penetrate the skin as easily as possible. Each hollow microneedle has at least one passage or channel or at least one bore, which extends from the base of the microneedle to the tip of the microneedle or to approximately the tip of the microneedle. The passages preferably have a round diameter.

The microneedles may have a shaft with a round cross-section or a non-round cross-section, for example with a triangular, square or a polygonal cross-section. The shaft may have one or more passages that runs/run from the base of the needle to the tip or approximately to the tip of the needle. The microneedles may be designed as (barb) hooks, with one or more of these microneedles having one or more such hooks. Furthermore, the microneedles may be helically shaped and rotatably arranged, thereby facilitating penetration into the skin when a rotating movement is applied and causing an anchoring in the skin (DE 103 53 629 A1), in particular at the desired penetration depth in the epidermis.

The diameter of a microneedle is usually between 1 μm and 1000 μm, preferably between 10 μm and 100 μm. The diameter of a passage is usually between 3 μm and 80 μm and is suitable for the passage of preferably liquid substances, solutions and substance preparations. The length of a microneedle is usually between 5 μm and 6,000 μm, in particular between 100 μm and 700 μm.

The microneedles, by means of their base, are attached to a flat carrier or integrated into a flat carrier. The microneedles are preferably arranged substantially perpendicular to the surface of the carrier. The microneedles can be arranged in a regular or irregular pattern. An arrangement of a plurality of microneedles can comprise microneedles with different cross-sectional shapes, different diameters and/or different lengths. For example, the arrangement of a plurality of microneedles may comprise exclusively hollow microneedles.

The microneedle array may have a flat carrier, wherein the carrier has substantially a disc-like, plate-like or film-like basic shape. The carrier may have a round, oval, triangular, square or polygonal base area. The carrier may be made of different materials, such as a metal, a ceramic material, a semiconductor, an organic material, a polymer or a composite.

In another preferred embodiment, the following substances are preferred in addition to PVP in a formulation for the production of the microneedles which consist of or comprise same: disaccharide, preferably trehalose, non-ionic surfactants, preferably polysorbate (ethoxylated sorbitan fatty acid esters, such as Tween), polyalcohol, in particular glycerol (glycerin).

TABLE 1

| Substance \| Name | Function | Concentration/Dose in % by weight |
|---|---|---|
| HBsAg/Vaccine antigen | Active substance/vaccine | 0.1 μg to 100 μg per MNA |
| polyvinylpyrrolidone (PVP) | Auxiliary | 1% to 95% (m/m) |
| Trehalose | Auxiliary | 0.1% to 50% (m/m) |
| Polysorbate | Auxiliary | 0.01% to 10% (m/m) |
| Glycerol | Auxiliary | 0.1% to 10% (m/m) |
| Water | Solvent | 20% to 95% (m/m) |

After drying of the liquid formulation, for example to form a microneedle array (MNA) with 1-20% (m/m) residual water content, the composition of the MNA is changed accordingly by the water loss.

Therefore, the invention relates to a microneedle array or product, in particular a medicinal product, for use in the intradermal application for hepatitis vaccination, wherein a formulation contains up to 95% by weight of polyvinylpyrrolidone, in particular 0.1% by weight to 50% by weight of trehalose, in particular 0.01% by weight to 10% by weight of polysorbate, in particular 0.1% by weight to 10% by weight of glycerol.

Furthermore, it is particularly advantageous that the MNAs according to the invention can do without adjuvants (see FIG. 1).

EXAMPLES AND DRAWINGS

A Brief Description of the Figure

The FIGURE illustrates a preclinical in-vivo study (guinea pigs), the above formulation showed excellent results of the resulting antibody titres in the blood of the vaccinated animals after application of the micro (needle) array patches (MAP).

For the production of the microneedles according to the invention, the known methods can be applied, such as McCrudden M T, Alkilani A Z, McCrudden C M, McAlister E, McCarthy H O, Woolfson A D, et al. Design and physicochemical characterisation of novel dissolving polymeric microneedle arrays for transdermal delivery of high dose, low molecular weight drugs. J Control Release. 2014; 180: 71-80.

In a preclinical in-vivo study (guinea pigs), the above formulation showed excellent results of the resulting antibody titres in the blood of the vaccinated animals after application of the micro(needle)array patches (MAP); see FIG. 1.

The study design includes a prime/boost/boost (0/1/3 months) in 4 groups×12 animals, of which 3 are MAP groups with (20/40/60 μg HBsAg/MNA) and one is a reference group with intramuscular injection, i.m. with 20 μg HBsAg/i.m.). The primary endpoint is 4 months with follow-up titres after 6 and 12 months.

The results of the study show that in all MNA and injection groups a sufficiently strong (>red line) formation of anti-HBsAg antibodies serologically relevant for the evaluation of the vaccination success was achieved.

Furthermore, the experimental groups did not show any relevant differences between adjuvant (see FIG. 1, hatched) and non-adjuvant formulations (see FIG. 1, not hatched), as well as intradermal administration of the antigen by means of microarray and conventional application by injection needle.

The invention claimed is:

1. A microneedle array for use in the intradermal application for hepatitis vaccination, wherein the microneedle array consists of HBsAg, and 1 to 95% by weight of polyvinylpyrrolidone and
trehalose 0.1 to 50% by weight as an auxiliary
polysorbate 0.01 to 10% by weight as an auxiliary and
glycerol 0.1 to 10% by weight as an auxiliary.

2. The microneedle array according to claim 1, wherein the HBsAg content is 0.1 μg to 100 μg per microneedle array.

3. A product comprising the microneedle array according to claim 1 for use in the intradermal application for hepatitis vaccination.

4. A medicinal product comprising the microneedle array according to claim 1 for use in the intradermal application for hepatitis vaccination.

5. A product for use in the intradermal application for hepatitis vaccination, wherein the product comprises the microneedle array according to claim 1 and an applicator together with triggering device.

6. A method comprising performing an intradermal application for vaccination of HbsAg antigen utilizing the microneedle array according to claim 1.

7. A microneedle array for use in the intradermal application for hepatitis vaccination, wherein the microneedle array consists of HBsAg and
trehalose 0.1 to 50% by weight
polysorbate 0.01 to 10% by weight as an auxiliary
glycerol 0.1 to 10% by weight and
a carrier made of a ceramic material or a semiconductor.

8. A device comprising:
a microneedle array consisting of HBsAg and
polyvinylpyrrolidone 1 to 95% by weight,
trehalose 0.1 to 50% by weight
polysorbate 0.01 to 10% by weight as an auxiliary and
glycerol 0.1 to 10% by weight; and
an applicator together with a plunger and a triggering device and wherein the triggering device comprises a pump, a syringe or a spring, so that the plunger impact with sufficient energy can be implemented and the microneedles have different diameters and/or different lengths.

9. The microneedle array according to claim 1, wherein microneedles have a shaft with a triangular or a polygonal cross-section.

10. The microneedle array according to claim 1, wherein one or more of the microneedles having barb hooks.

11. The microneedle array according to claim 1, wherein the microneedles are helically shaped and rotatably arranged.

12. The microneedle array according to claim 1, wherein the microneedle has a diameter between 10 μm and 100 μm.

13. The microneedle array according to claim 8, wherein the microneedles have different diameters.

* * * * *